(12) United States Patent
Anker et al.

(10) Patent No.: US 10,745,305 B2
(45) Date of Patent: Aug. 18, 2020

(54) METHODS AND DEVICES FOR PERFORMING REACTIONS

(71) Applicant: Ariel Scientific Innovations Ltd., Ariel (IL)

(72) Inventors: Yaakov Anker, Salit (IL); Alexander Gimburg, Itamar (IL)

(73) Assignee: Ariel Scientific Innovations Ltd., Ariel (IL)

( * ) Notice: Subject to any disclaimer, the term of this patent is extended or adjusted under 35 U.S.C. 154(b) by 242 days.

(21) Appl. No.: 15/736,421

(22) PCT Filed: Jul. 7, 2016

(86) PCT No.: PCT/IB2016/054096
§ 371 (c)(1),
(2) Date: Dec. 14, 2017

(87) PCT Pub. No.: WO2017/006285
PCT Pub. Date: Jan. 12, 2017

(65) Prior Publication Data
US 2018/0186669 A1    Jul. 5, 2018

Related U.S. Application Data

(60) Provisional application No. 62/190,262, filed on Jul. 9, 2015.

(30) Foreign Application Priority Data

Mar. 29, 2016    (GB) .................................. 1605191.4

(51) Int. Cl.
*C02F 3/00*      (2006.01)
*C12M 1/00*    (2006.01)
(Continued)

(52) U.S. Cl.
CPC ............ *C02F 3/006* (2013.01); *B01F 3/0451* (2013.01); *B01F 5/0212* (2013.01); *B01F 5/043* (2013.01);
(Continued)

(58) Field of Classification Search
CPC .... B01F 7/00633; B01F 7/18; B01F 15/0283; B01F 2013/1091; C02F 1/5281; B01J 19/006; B01J 19/0066; B01J 19/18
See application file for complete search history.

(56) References Cited

U.S. PATENT DOCUMENTS 4,117,048 A * 9/1978 Stockner ............. B01F 3/04539
  261/93
4,193,950 A 3/1980 Stockner et al.
(Continued)

FOREIGN PATENT DOCUMENTS

CN    201864727 U    6/2011
CN    204672151      9/2015
(Continued)

OTHER PUBLICATIONS

Combined Search and Examination Report for Application GB 1605191.4, dated Apr. 21, 2016.
(Continued)

*Primary Examiner* — Ana M Fortuna
(74) *Attorney, Agent, or Firm* — The Law Office of Joseph L. Felber

(57) ABSTRACT

Disclosed are devices suitable for performing chemical and/or biological reactions. Also disclosed are methods of simultaneously performing at least two chemical and/or biological reactions under different conditions in a single reaction chamber.

36 Claims, 3 Drawing Sheets

(51) Int. Cl.
*C02F 3/28* (2006.01)
*C02F 3/30* (2006.01)
*B01J 19/00* (2006.01)
*B01J 19/18* (2006.01)
*B01J 4/00* (2006.01)
*B01F 5/02* (2006.01)
*B01F 5/04* (2006.01)
*B01F 3/04* (2006.01)
*C02F 103/00* (2006.01)
*C02F 103/20* (2006.01)

(52) U.S. Cl.
CPC ........... *B01J 4/002* (2013.01); *B01J 19/0066* (2013.01); *B01J 19/18* (2013.01); *C02F 3/2806* (2013.01); *C02F 3/301* (2013.01); *C12M 29/06* (2013.01); *B01J 2219/00076* (2013.01); *B01J 2219/00135* (2013.01); *B01J 2219/00177* (2013.01); *C02F 2103/005* (2013.01); *C02F 2103/20* (2013.01); *C02F 2203/006* (2013.01); *C02F 2209/001* (2013.01); *C02F 2209/02* (2013.01); *C02F 2209/06* (2013.01); *C02F 2209/40* (2013.01)

(56) References Cited

U.S. PATENT DOCUMENTS

| | | |
|---|---|---|
| 5,268,094 A | 12/1993 | Long |
| 5,409,610 A | 4/1995 | Clark |
| 5,650,070 A | 7/1997 | Pollock |
| 8,876,369 B1 * | 11/2014 | Lott ..................... B01F 7/16 |
| | | 366/328.2 |
| 9,771,287 B2 * | 9/2017 | Anker ................... C02F 3/302 |
| 2006/0138046 A1 | 6/2006 | Stafford |
| 2007/0053238 A1 * | 3/2007 | Kocienski ............ B01F 7/186 |
| | | 366/273 |
| 2007/0264156 A1 * | 11/2007 | Yamakawa ............ G01N 35/02 |
| | | 422/63 |

FOREIGN PATENT DOCUMENTS

| | | |
|---|---|---|
| GB | 2535659 | 2/2017 |
| SU | 956559 | 9/1982 |

OTHER PUBLICATIONS

International Search Report and Written Opinion for PCT/IB2016/054096, dated Sep. 29, 2016.

* cited by examiner

METHODS AND DEVICES FOR PERFORMING REACTIONS

RELATED APPLICATIONS

The present application gains priority from U.S. Provisional Patent Application No. 62/190,262 filed 9 Jul. 2015 and also from UK Patent Application No. GB 1605191.4 filed 29 Mar. 2016, both which are included by reference as if fully set-forth herein.

FIELD AND BACKGROUND OF THE INVENTION

The invention, in some embodiments, relates to the field of chemical and biological processes. In some embodiments, the invention relates to the field of wastewater processing. In some embodiments, the invention relates to the field of chemical reactors.

Chemical and biological processes are often performed in one or more vessels (reactors). Methods and devices suitable for performing chemical and biological processes are sought after.

For example, it is known to use microbial digestion to process wastewater. Methods and devices suitable for wastewater processing by microbial digestion that have advantages over known such methods and devices are sought after.

It is known to use Venturi pumps in the field of chemical and biological reactions, see for example, U.S. Pat. No. 4,193,950, Soviet patent application SU 956559-A1 and China utility model publication CN204672151-U.

SUMMARY OF THE INVENTION

Some embodiments of the invention herein provide methods and devices for performing chemical and biological reactions (e.g., chemical reactions, microbial digestion of wastewater) in a vessel. In some such embodiments, a vessel is provided that allows definition of two or more volumes inside the same chamber of such a vessel, where the reaction conditions of each such volume are independently controllable.

Thus, according to an aspect of some embodiments of the teachings herein, there is provided a device suitable for performing chemical and/or biological reactions, comprising:
 a. a vessel defining at least one reaction chamber configured for holding liquids, the chamber having an upper portion, a lower portion and a vertical axis (when in use);
 b. at least one chamber inlet providing fluid communication into the chamber from outside the chamber;
 c. at least one chamber outlet providing fluid communication from inside the chamber to outside the chamber;
 d. an upper mixing assembly located inside the chamber; and
 e. a lower mixing assembly located inside the chamber, positioned below the upper mixing assembly,
each mixing assembly comprising a Venturi pump having a motive fluid inlet, an aspirate inlet and a Venturi pump outlet, the Venturi pump configured for accepting liquid contents of a corresponding portion (upper or lower portion) of the chamber into the motive fluid inlet as motive fluid, and to expel fluid out through the Venturi pump outlet back into the corresponding portion of the chamber. The upper mixing assembly is thus configured when operated to allow circulation of liquid in the upper portion of the chamber without substantially circulating liquid in the lower portion of the chamber and the lower mixing assembly is thus configured when operated to allow circulation of liquid in the lower portion of the chamber without substantially circulating liquid in the upper portion of the chamber. Such configuration allows the definition of independently-controllable reaction conditions in the upper portion and in the lower portion of the chamber of the vessel, thereby allowing simultaneously performing at least two chemical and/or biological reactions (one reaction in the upper portion, the other reaction in the lower portion) under different conditions in the reaction chamber.

Typically, the reaction chamber is a single continuous volume inside the vessel with no substantial physical partition that defines a border between the upper portion and the lower portion of the chamber.

In some embodiments, when both the upper and lower mixing assembly are operated, there is an intervening portion in the chamber located between the upper portion and the lower portion in which fluid is not substantially circulated when the mixing assemblies are operated.

As discussed herein in greater detail, in some preferred embodiments, the upper mixing assembly and the lower mixing assembly are independently operable, e.g., allowing operation and/or control of the first mixing assembly independently of operation and/or control of the second mixing assembly.

In some embodiments, the chamber has a height greater than greatest width (e.g., diameter). In some such embodiments, the chamber is cylindrical. In some such embodiments, the chamber is prismatic. In some such embodiments, the chamber is substantially a cone. In some such embodiments, the chamber is a truncated cone.

In some embodiments, at least one chamber inlet provides fluid communication from outside the chamber to inside the upper portion of the chamber. Additionally or alternatively, in some embodiments, at least one chamber inlet provides fluid communication from outside the chamber to inside the lower portion of the chamber. In some embodiments, the device is provided with a second (or more) inlet that provides fluid communication from outside the chamber to inside the chamber. Multiple inlets allow addition of liquid for reaction into a specific portion of the chamber.

In some embodiments, at least one chamber outlet provides fluid communication from inside the lower portion of the chamber to outside the chamber.

In some embodiments, at least one chamber outlet provides fluid communication from inside the upper portion of the chamber to outside the chamber.

In some embodiments, at least one Venturi pump outlet is directed perpendicularly to the vertical axis of the chamber. In some such embodiments, all Venturi pump outlets of the device are directed perpendicularly to the vertical axis of the chamber. In some embodiments, at least one Venturi pump outlet is directed parallel to the vertical axis of the chamber, e.g., vertically upwards or vertically downwards. In some such embodiments, all Venturi pump outlets of the device are directed parallel to the vertical axis of the chamber.

In some embodiments, the Venturi pumps are immobile, that is to say, during operation remain in a fixed location inside the vessel.

In some embodiments, the device further comprises at least one liquid-driving pump functionally associated with the upper mixing assembly, the at least one liquid-driving pump configured to drive liquid contents of the chamber into a motive fluid inlet of a Venturi pump of the upper mixing assembly. In some embodiments, the liquid-driving pump functionally associated with the upper mixing assembly is an immersible liquid pump located inside the chamber. In some embodiments, at least one of the liquid-driving pumps functionally associated with the upper mixing assembly is not functionally associated with the lower mixing assembly thereby allowing operation of the upper mixing assembly independently of the lower mixing assembly by activation of that liquid-driving pump.

In some embodiments, the device comprises at least one liquid-driving pump functionally associated with the lower mixing assembly, the at least one liquid-driving pump configured to drive liquid contents of the chamber into a motive fluid inlet of a Venturi pump of the lower mixing assembly. In some embodiments, the liquid-driving pump functionally associated with the lower mixing assembly is an immersible liquid pump located inside the chamber. In some embodiments, at least one of the liquid-driving pumps functionally associated with the lower mixing assembly is not functionally associated with the upper mixing assembly thereby allowing operation of the lower mixing assembly independently of the upper mixing assembly by activation of that liquid-driving pump. In some embodiments where the device comprises at least one liquid-driving pump functionally associated with the upper mixing assembly, at least one of the at least one liquid-driving pump associated with the upper mixing assembly is also at least one of the at least one liquid-driving pump associated with the lower mixing assembly.

In some embodiments where the device comprises at least one liquid-driving pump functionally associated with the upper mixing assembly, the device further comprises a controllable valve having at least two states:
  an open state allowing flow of liquid from the liquid-driving pump to the motive fluid inlet of a Venturi pump of the lower mixing assembly; and
  a closed state preventing flow of liquid from the liquid-driving pump to the motive fluid inlet of the Venturi pump of the lower mixing assembly.
In some embodiments, such a controllable valve allows operation of the lower mixing assembly independently of the upper mixing assembly by selection of the state of the controllable valve.

In some embodiments, the device further comprises a controllable valve having at least two states:
  an open state allowing flow of liquid from the liquid-driving pump to the motive fluid inlet of the Venturi pump to the upper mixing assembly; and
  a closed state preventing flow of liquid from the liquid-driving pump to the motive fluid inlet of the Venturi pump to the upper mixing assembly.
In some embodiments, such a controllable valve allows operation of the upper mixing assembly independently of the lower mixing assembly by selection of the state of the controllable valve.

In some embodiments, at least one of the at least one liquid-driving pump associated with the upper mixing assembly is different from at least one of the at least one liquid-driving pump associated with the lower mixing assembly. In some such embodiments, each one of the two mixing assemblies has a set of dedicated liquid-driving pumps, that is to say, all of the liquid-driving pumps associated with the upper mixing assembly are different from all of the liquid driving pumps associated with the lower mixing assembly.

In some embodiments, at least one liquid-driving pump associated with the upper mixing assembly and at least one liquid-driving pump associated with the lower mixing assembly are separately operable (i.e., activatable). In some embodiments, such separately operability allows operation of the lower mixing assembly independently of the upper mixing assembly by operation of a liquid-driving pump associated only with the lower mixing assembly. In some embodiments, such separately operability allows operation of the upper mixing assembly independently of the lower mixing assembly by operation of a liquid-driving pump associated only with the upper mixing assembly.

In some embodiments, the liquid-driving pumps are electrically-powered pumps. In some such embodiments, an alternating current power supply to the pumps is functionally associated with a frequency converter, allowing to change the rate of pumping of the pumps.

In some embodiments, the device further comprises a gas line in fluid communication with an aspirate inlet of a Venturi pump of the upper mixing assembly. In some embodiments, the gas line provides fluid communication between an aspirate inlet of a Venturi pump of the upper mixing assembly and the open air. In some embodiments, the device further comprises a gas inlet valve functionally associated with the gas line, having at least two states:
  a closed state preventing flow of gas through the gas line to an aspirate inlet of a Venturi pump of the upper mixing assembly; and
  an open state allowing flow of gas through the gas line to an aspirate inlet of a Venturi pump of the upper mixing assembly.
In some embodiments, such a gas inlet valve allows allowing, preventing and/or regulating the inflow of gas into the upper portion of the chamber by selection of the appropriate valve state.

In some embodiments, the device further comprises a gas reagent reservoir in fluid communication with an aspirate inlet of a Venturi pump of the upper mixing assembly, in some embodiments a pressurized gas reagent reservoir, in some embodiments through a gas line as (e.g., as described above), in some embodiments through a valve (e.g., analogous or identical to the gas inlet valve described above).

In some embodiments, the device further comprises a liquid reagent reservoir in fluid communication with an aspirate inlet of a Venturi pump of the upper mixing assembly, in some embodiments through a liquid reagent line, in some embodiments through a valve having at least two states: a closed state preventing flow of liquid reagent from the liquid reagent reservoir through the liquid reagent line to an aspirate inlet of the Venturi pump of the upper mixing assembly; and an open state allowing flow of liquid reagent from the liquid reagent reservoir through the liquid reagent line to an aspirate inlet of the Venturi pump of the upper mixing assembly. In some embodiments, such a valve allows allowing, preventing and/or regulating the inflow of liquid reagent into the upper portion of the chamber by selection of the appropriate valve state.

In some embodiments, the device further comprises a liquid reagent reservoir in fluid communication with an aspirate inlet of a Venturi pump of the upper mixing assembly through a gas line as described above.

In some embodiments, the device further comprises a gas line in fluid communication with an aspirate inlet of a Venturi pump of the lower mixing assembly. In some embodiments, the gas line provides fluid communication between the aspirate inlet of the Venturi pump of the lower mixing assembly and the open air. In some embodiments, the device further comprises a gas inlet valve functionally associated with the gas line, having at least two states:

a closed state preventing flow of gas through the gas line to an aspirate inlet of the Venturi pump of the lower mixing assembly; and an open state allowing flow of gas through the gas line to an aspirate inlet of the Venturi pump of the lower mixing assembly.

In some embodiments, such a gas inlet valve allows allowing, preventing and/or regulating the inflow of gas into the lower portion of the chamber by selection of the appropriate valve state.

In some embodiments, the device further comprises a gas reagent reservoir in fluid communication with an aspirate inlet of a Venturi pump of the lower mixing assembly, in some embodiments a pressurized gas reagent reservoir, in some embodiments through a gas line as (e.g., as described above, in some embodiments through a valve (e.g., analogous or identical to the gas inlet valve described above).

In some embodiments, the device further comprises a liquid reagent reservoir in fluid communication with an aspirate inlet of the Venturi pump of the lower mixing assembly, in some embodiments through a liquid reagent line, in some embodiments through a valve having at least two states: a closed state preventing flow of liquid reagent from the liquid reagent reservoir through the liquid reagent line to an aspirate inlet of the Venturi pump of the lower mixing assembly; and an open state allowing flow of liquid reagent from the liquid reagent reservoir through the liquid reagent line to an aspirate inlet of the Venturi pump of the lower mixing assembly. In some embodiments, such a valve allows allowing, preventing and/or regulating the inflow of liquid reagent into the lower portion of the chamber by selection of the appropriate valve state.

In some embodiments, the device further comprises a liquid reagent reservoir in fluid communication with an aspirate inlet of the Venturi pump of the lower mixing assembly through a gas line as described above.

In some embodiments, the device further comprises an upper temperature controller, located within or in immediate proximity (e.g., on the walls of the chamber) to the upper portion of the chamber to control the temperature of the liquid contents of the chamber located in proximity of the upper mixing assembly without substantially affecting the temperature of the contents of the chamber located in proximity of the lower mixing assembly. In some such embodiments, the upper temperature controller comprises a heating component, located within or in immediate proximity to the upper portion of the chamber to heat liquid contents of the chamber located in proximity of the upper mixing assembly without substantial heating of contents of the chamber located in proximity of the lower mixing assembly. In some such embodiments, the upper temperature controller comprises a cooling component, located within or in immediate proximity to the upper portion of the chamber to cool liquid contents of the chamber located in proximity of the upper mixing assembly without substantial cooling of contents of the chamber located in proximity of the lower mixing assembly. In some such embodiments, the upper temperature controller comprises both such a heating component and such a cooling component. In some embodiments, the device further comprises an upper heater as the temperature controller, located within or in immediate proximity to the upper portion of the chamber to heat liquid contents of the chamber located in proximity of the upper mixing assembly without substantial heating of contents of the chamber located in proximity of the lower mixing assembly.

In some embodiments, the upper temperature controller is configured to control the temperature of liquid contents of the chamber that are to exit a Venturi pump outlet of the upper mixing assembly, e.g., the heating or cooling is through the Venturi pump, the liquid-driving pump or a conduit therebetween.

In some embodiments, the device further comprises a lower temperature controller, located within or in immediate proximity (e.g., on the walls of the chamber) to the lower portion of the chamber to control the temperature of the liquid contents of the chamber located in proximity of the lower mixing assembly without substantially effecting the temperature of the contents of the chamber located in proximity of the upper mixing assembly. In some such embodiments, the lower temperature controller comprises a heating component, located within or in immediate proximity to the lower portion of the chamber to heat liquid contents of the chamber located in proximity of the lower mixing assembly without substantial heating of contents of the chamber located in proximity of the upper mixing assembly. In some such embodiments, the lower temperature controller comprises a cooling component, located within or in immediate proximity to the lower portion of the chamber to cool liquid contents of the chamber located in proximity of the lower mixing assembly without substantial cooling of contents of the chamber located in proximity of the upper mixing assembly. In some such embodiments, the lower temperature controller comprises both such a heating component and such a cooling component. In some embodiments, the device further comprises a lower heater as the temperature controller, located within or in immediate proximity to the lower portion of the chamber to heat liquid contents of the chamber located in proximity of the lower mixing assembly without substantial heating of contents of the chamber located in proximity of the upper mixing assembly.

In some embodiments, the lower temperature controller is configured to control the temperature of liquid contents of the chamber that are to exit a Venturi pump outlet of the lower mixing assembly, e.g., the heating or cooling is through the Venturi pump, the liquid-driving pump or a conduit therebetween.

According to an aspect of some embodiments of the invention, there is also provided a method of simultaneously performing at least two chemical and/or biological reactions under different conditions in a single reaction chamber, comprising:

placing a device as described herein so that the vertical axis of the device is at an angle within 45° of parallel to the gravity vector (as depicted in the Figures) so that the upper portion of the chamber is above the lower portion of the chamber (in some embodiments, immediately above);

placing at least one liquid inside the reaction chamber of the vessel so that both the upper portion and the lower portion contain a liquid; and performing at least one of:

operating the upper mixing assembly to circulate the liquid in the upper portion of the chamber without substantially circulating liquid in the lower portion of the chamber; and operating the lower mixing assembly to circulate the liquid in the lower portion of the chamber without substantially circulating liquid in the upper portion of the chamber, thereby performing a first reaction (e.g., a chemical and/or biological reaction) in the upper portion of the reaction chamber and a second reaction (e.g., a chemical and/or biological reaction) in the lower portion of the reaction chamber, wherein conditions of the first reaction are different than the conditions of the second reaction.

In some embodiments, the angle is within 30°, within 25°, within 20°, within 15°, within 10° and even within 5° of parallel to the gravity vector.

In some embodiments, the liquid in the upper portion comprises a solvent with reagents. In some embodiments, the liquid in the upper portion comprises an organic solvent. In some embodiments, the liquid in the upper portion comprises an aqueous solvent. In some embodiments, the liquid in the upper portion is wastewater so that the solvent is water and the reagents are waste to be digested.

In some embodiments, the liquid in the lower portion comprises a solvent with reagents. In some embodiments, the liquid in the lower portion comprises an organic solvent. In some embodiments, the liquid in the lower portion comprises an aqueous solvent. In some embodiments, the liquid in the lower portion is wastewater so that the solvent is water and the reagents are waste to be digested.

In some embodiments, the liquid in the upper portion has a different gas content (e.g., oxygen content) than the liquid in the lower portion. For example, in some embodiments aerobic digestion of wastewater is performed in the upper portion of the chamber while anaerobic or anoxic digestion of wastewater is performed in the lower portion of the chamber.

In some embodiments, the liquid in the upper portion of the chamber has a different density than the liquid in the lower portion of the chamber.

In some embodiments, the first mixing assembly and the second mixing assembly are operated in a different manner, thereby leading to the different reaction conditions in the upper portion and the lower portion. In some embodiments, the different operation comprises at least one of:
- addition of a different liquid to one of the upper portion and the lower portion (in some embodiments through the respective mixing assemblies);
- addition of a different gas to one of the upper portion and the lower portion (in some embodiments through the respective mixing assemblies); and
- maintaining a temperature in the upper portion different than a temperature in the lower portion.

Some embodiments of the invention herein provide methods and devices for processing wastewater using microbial digestion. Accordingly, in some embodiments, the at least one reaction chamber is a digestion chamber configured for holding wastewater and suitable for containing microbial digestion of wastewater as a reaction. In some such embodiments, the device further comprises a solid bacterial growth support inside at least part of the digestion chamber, in some embodiments, substantially all of the digestion chamber.

In some embodiments, phase-transfer reactions are performed in a device according to the teachings herein where the denser phase is located in the lower portion of the chamber around the lower mixing assembly, and the less dense phase is located in the upper portion of the chamber around the upper mixing assembly. In some such embodiments, the denser phase is aqueous and the less dense phase is organic (e.g., comprises a solvent having a density less than 1, such as oil or petrol ether). In some such embodiments, the less dense phase is aqueous and the denser phase is organic (e.g., comprises a solvent having a density greater than 1, such as dichloromethane). In some such embodiments, the denser phase is an aqueous solution of high density (e.g., concentrated brine) and the less dense phase is aqueous with a lower density.

Unless otherwise defined, all technical and scientific terms used herein have the same meaning as commonly understood by one of ordinary skill in the art to which the invention pertains. In case of conflict, the specification, including definitions, takes precedence.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
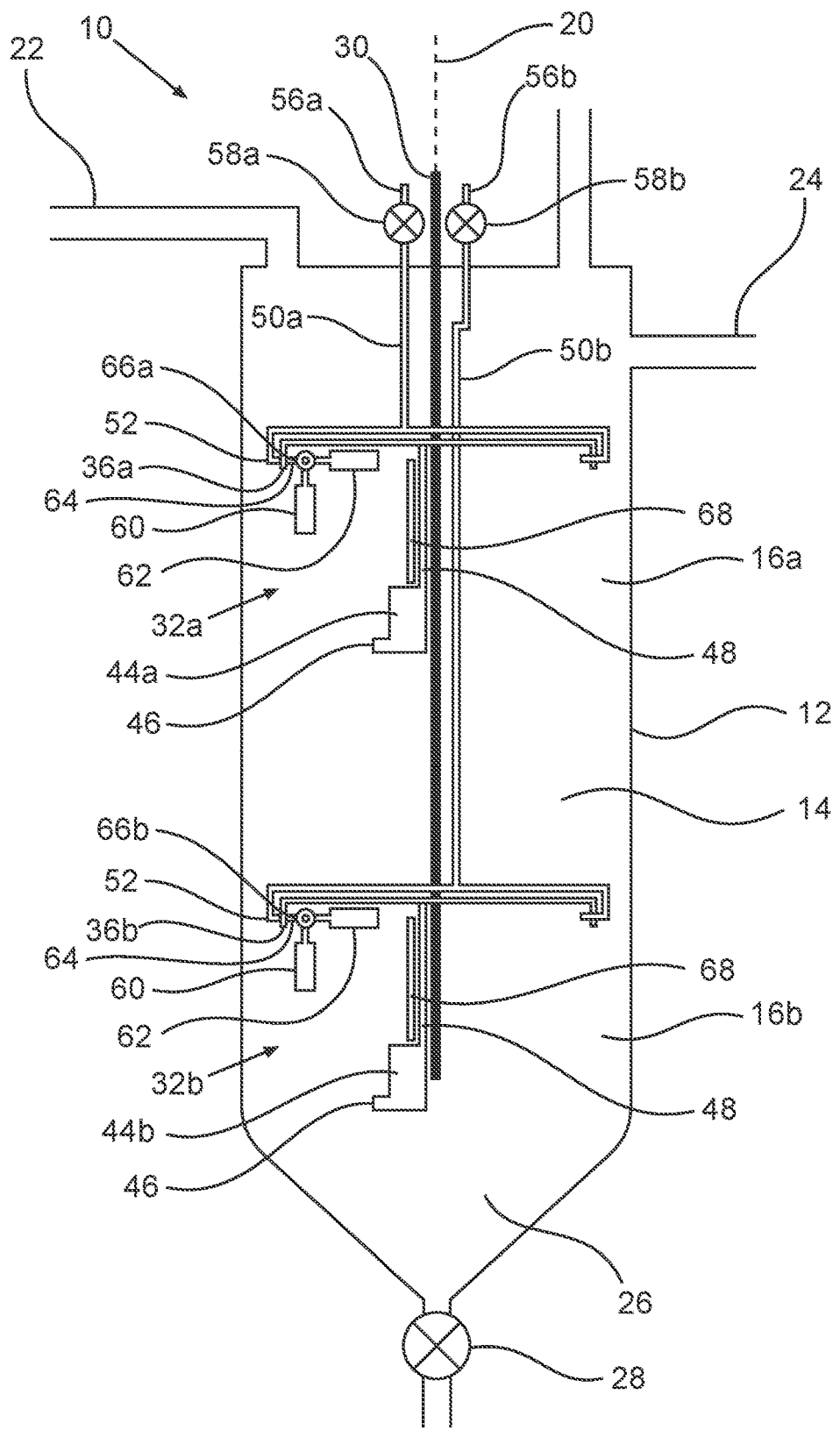
FIG. 1 is a schematic depiction of an embodiment of a device according to the teachings herein in side cross section.

Some embodiments of the invention herein provide methods and devices suitable for performing chemical and/or biological reactions, in some embodiments, processing wastewater using microbial digestion.

Specifically, some embodiments of the teachings herein provide methods and devices allowing simultaneously performing, in one vessel, chemical and/or biological reactions in liquid environments under two different conditions in two distinct and volumes of the vessel. In some such embodiments, the liquid environments in each of the distinct volumes are immiscible (e.g., organic and aqueous liquids). In some such embodiments, the liquid environments in each of the distinct volumes are miscible but have substantially different densities (e.g., brine and non-brine water). In some such embodiments, the liquid environments in each of the distinct volumes are miscible.

Specifically, some embodiments of the teachings herein provide methods and devices suitable for microbial digestion that include a vessel defining at least one chamber that allows performance of aerobic, anaerobic and anoxic modes of digestion of wastewater in one chamber, sequentially or simultaneously.

Some embodiments of the method and device obviate the need for multiple vessels to perform SBR (sequential bioreactor) digestion.

In some embodiments, the use of a single vessel saves space, resources (maintenance and energy), processing time, and is relatively simple to produce, factors that are extremely important in the field of environmentally-friendly wastewater processing.

Some embodiments allow use of preferred conditions for each mode of digestion, for example, by allowing selective heating and/or selective addition of reagents (e.g., bacteria, nutrients, pH modifiers, feedstock for increased production of desired gases, e.g. combustible biogases), for example, allowing greater generation of methane-forming bacteria by controlling the temperature and pH of anaerobic digestion.

Some embodiments allow anaerobic and anoxic modes of digestion to be performed without use of sealed vessels and/or scrubbers.

Embodiments of the teachings herein are suitable for processing various types of wastewater, including blackwater and agricultural manure slurry.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

An embodiment of a device according to the teachings herein, device 10 is schematically depicted in side cross section in FIG. 1. Device 10 is configured for processing of wastewater using microbial digestion.

Device 10 comprises a vessel 12 defining a reaction chamber 14 that is a digestion chamber configured for holding wastewater, chamber 14, when in use, having an upper portion 16a, a lower portion 16b and a vertical axis 20. Chamber 14 is a cylinder with a height greater than diameter. A chamber inlet 22 provides fluid communication from outside chamber 14 to inside upper portion 16a of chamber 14, allowing addition of wastewater for processing into chamber 14. A chamber outlet 24 provides fluid communication from inside chamber 14 to outside chamber 14, allowing removal of water that has been sufficiently processed from upper portion 16a of chamber 14.

In some embodiments, at least part of chamber 14 (e.g., one or both of upper portion 16a and lower portion 16b) comprises a solid bacterial growth support (fixed growth media), allowing development of sessile microbes.

At the bottom of chamber 14 there is a converging (conical) sludge-accumulation portion 26 provided with a sludge valve 28 allowing removal of accumulated sludge from chamber 14.

Passing coaxially through chamber 14 is a support bar 30 of stainless steel to which are secured an upper mixing assembly 32a within upper portion 16a and a lower mixing assembly 32b positioned below upper mixing assembly 32a within lower portion 16b.

Each one of mixing assemblies 32a and 32b comprise four Venturi pumps (a total of eight Venturi pumps in device 10), four of which are depicted in FIG. 1. In FIG. 1, one of the Venturi pumps of mixing assembly 32a is labeled 36a and one of the Venturi pumps of mixing assembly 32b is labeled 36b.

Figure 2:
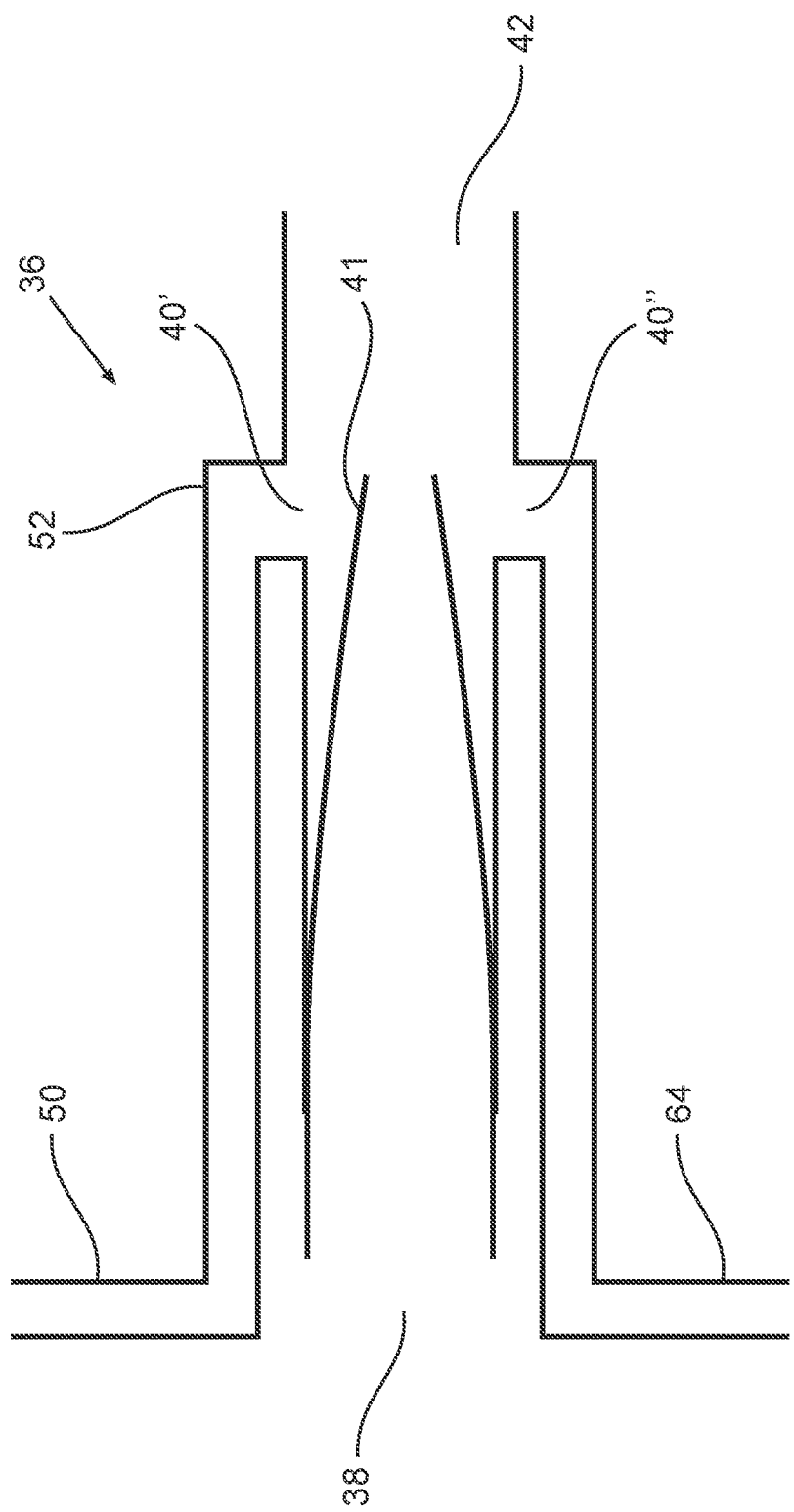
FIG. 2 is a schematic depiction of an embodiment of a Venturi pump suitable for implementing some embodiments of the teachings herein in side cross section.

In FIG. 2, a Venturi pump 36 (identical to Venturi pumps 36a and 36b) is schematically depicted in side cross section, having a motive fluid inlet 38, aspirate inlets 40' and 40" and a Venturi pump outlet 42.

The Venturi pumps (e.g., 36a and 36b) of device 10 are configured for accepting liquid contents of chamber 14 into motive fluid inlet 38 as motive fluid. As the moving motive fluid passes a Venturi nozzle 41 and out through Venturi pump outlet 42, fluid (such as a gas or liquid) is drawn into aspirate inlets 40' and 40" in accordance with the Bernoulli principle to mix with the moving motive fluid.

In mixing assemblies 32a and 32b, Venturi pump outlets 42 of the Venturi pumps (e.g., 36a and 36b) are directed downwardly parallel to vertical axis 20 of chamber 14.

Each of mixing assemblies 32a and 32b further comprises an associated liquid-driving pump 44a and 44b, respectively, each pump 44a and 44b having an associated pump inlet 46.

Each liquid-driving pump 44a or 44b is functionally associated with the four Venturi pumps of a respective mixing assembly 32a or 32b. Specifically, each one of liquid-driving pumps 44a and 44b is configured to draw liquid contents of a corresponding portion 16a and 16b (respectively) of chamber 14 into a respective pump inlet 46 and drive the drawn liquid through a conduit 48 into motive fluid inlets 38 of the associated Venturi pumps (e.g., 36a and 36b).

Any suitable liquid-driving pumps may be used in implementing the teachings herein. In some embodiments, the liquid-driving pumps are immersible pumps. In some embodiments, the liquid driving pumps are electrically-powered. In some embodiments, electrically-powered liquid-driving pumps receive direct-current electrical power. In some such embodiments, the power supply of each liquid-driving pump is functionally associated with a variable resistor, allowing an operator to set the rate of pumping of each one of the liquid-driving pumps independently. In device 10, liquid-driving pumps 44 are electrically-powered immersible pumps that receive alternating-current electrical power for operation by electrical cables (not depicted), the alternating current passing through a controllable frequency converter. Such configuration allows an operator to set the rate of pumping of each one of liquid-driving pumps 44a and 44b independently without excess stress on pumps 44.

Device 10 further comprises a gas line 50a that is in fluid communication with aspirate inlets 40' of the Venturi pumps associated with upper mixing assemblies 32a (e.g., Venturi pump 36a) and a gas line 50b that is in fluid communication with aspirate inlets 40' of the Venturi pumps associated with lower mixing assemblies 32b (e.g., Venturi pump 36b).

Specifically, as seen in FIG. 2, a distal end 52 of a gas line 50 covers an aspirate inlet 40' of Venturi pump 36. When a liquid enters Venturi pump 36 through motive fluid inlet 38 with sufficient velocity, the contents of gas line 50 are drawn into Venturi pump 36 through aspirate inlet 40'.

In device 10, a proximal end 56a and 56b of both gas lines 50a and 50b respectively emerges into the open air, thereby providing fluid communication between the aspirate inlets 40' of all eight Venturi pumps (including 36a and 36b) and the open air, so that when a respective liquid-driving pump 44a or 44b is activated to drive motive fluid into a motive fluid inlet 38 of respective Venturi pumps (e.g., 36a or 36b), atmospheric air is draw into a respective gas line 50*a* or 50*b* through distal ends 52 thereof to enter the Venturi pump 36 through the respective aspirate inlets 40' to be mixed with the motive fluid.

Device 10 further comprises electrically-controlled gas-inlet needle valves 58*a* and 58*b*, each functionally associated with one of the two gas lines 50*a* and 50*b*, respectively. Each gas-inlet valve 58*a* and 58*b* has:
- a closed state preventing flow of atmospheric air through a respective gas line 50*a* or 50*b* to aspirate inlets 40' of Venturi pumps of a respective mixing assembly 32*a* or 32*b*; and
- a plurality of open states, each such open state allowing flow of atmospheric air through a respective gas line 50*a* or 50*b* to aspirate inlets 40' of Venturi pump 36 of a respective mixing assembly 32*a* or 32*b*, where each open state is differentiated from the other open states by the degree that the valve 58*a* or 58*b* is open and therefore the rate that the air passes through a gas line 50 to the Venturi pumps.

Device 10 further comprises two gas reagent reservoirs 60 and two liquid reagent reservoirs 62, one reagent reservoir 60 and one liquid reagent reservoir 62 associated with each mixing assembly 32*a* or 32*b*, each such reservoir in fluid communication with an aspirate inlet 40" of a Venturi pump 36*a* or 36*b* through one of two reagent supply lines 64. Device 10 further comprises two electrically-controlled reagent valves 66*a* and 66*b* functionally associated with each one of the reagent supply lines 64 of one of the mixing assemblies 32*a* or 32*b* respectively, each reagent valve 66*a* and 66*b* having three states:
- a closed state preventing flow of reagent through an associated reagent supply line 64 to an aspirate inlet 40" of a respective Venturi pump 36*a* or 36*b* of a respective mixing assembly 32*a* or 32*b*;
- a first open state, allowing flow of gas reagent from an associated gas reagent reservoir 60 through an associated reagent supply line 64 to an aspirate inlet 40" of a respective Venturi pump 36*a* or 36*b* of a respective mixing assembly 32*a* or 32*b*; and
- a second open state, allowing flow of liquid reagent from an associated liquid reagent reservoir 62 through an associated reagent supply line 64 to an aspirate inlet 40" of a respective Venturi pump 36*a* or 36*b* of a respective mixing assembly 32*a* or 32*b*.

Covering a portion of each one of conduits 48 through which liquid flows from a liquid-driving pump 44*a* or 44*b* to Venturi pumps 36*a* or 36*b* is one of two electrical heating pads 68 configured, when activated, to heat liquid located inside conduit 48 that subsequently exits Venturi pump outlets 42. The two heating pads 68 are independently activatable. In such a way, each one of heating pads 68 is configured to heat the liquid contents of chamber 14 located in proximity of a respective mixing assembly 32*a* (liquid in upper portion 16*a*) or 32*b* (liquid in lower portion 16*b*) without substantial heating of contents of chamber 14 located in proximity of the other mixing assembly.

For use, digestion chamber 14 of vessel 12 of device 10 is filled with wastewater for processing, for example, black water or agricultural manure slurry through inlet 22 and then a wastewater processing mode is selected.

Full Aerobic Mode

In a first, all aerobic, mode, both liquid-driving pumps 44*a* and 44*b* are activated to operate the respective mixing assemblies 32*a* and 32*b* simultaneously and both gas inlet valves 58 are put in an open state. Substantially all the contents of chamber 14 are aerated and mixed by the action of the eight Venturi pumps (e.g., 36*a* and 36*b*), allowing for aerobic digestion thereof. Aerobic digestion is optionally aided by activating one or both heating pads 68 or by adding gas or liquid reagents by selectively opening reagent valves 66*a* and 66*b* as desired.

As known in the art, sufficient aerobic digestion yields water of sufficient purity to be removed from vessel 12 through outlet 24 for subsequent use or for disposal.

Full Anaerobic or Anoxic Mode

In a second, all anaerobic (or anoxic), mode, both liquid-driving pumps 44*a* and 44*b* are activated to operate the respective mixing assemblies 32*a* and 32*b* simultaneously and both gas inlet valves 58 are put in closed state. Substantially all the contents of chamber 14 are mixed by the action of the eight Venturi pumps (e.g., 36*a* and 36*b*) but since gas inlet valves 58*a* and 58*b* are closed, no air enters chamber 14. As the concentration of oxygen in the contents of chamber 14 is reduced due to the microbial digestion, the nature of the microbial population therein changes so that the proportion of aerobic microorganisms is reduced while the proportion of facultative and anaerobic microorganisms increases. As a result, the wastewater that is initially subject to aerobic digestion is eventually subject to anaerobic and even anoxic digestion. The anaerobic or anoxic digestion is optionally aided by activating one or both heating pads 68 or by adding gas or liquid reagents by selectively opening reagent valves 66 as desired. For example, to encourage methane-forming anaerobic bacteria instead of acid-forming anaerobic bacteria, it is preferred to control pH to be between 6.5 and 8 by addition of pH-modifying reagents and to control the temperature, where the exact temperature range depends on the desired species of methanogenic bacteria in the wastewater.

The full anaerobic or anoxic digestion mode is typically useful for reducing the amount of sludge that accumulates in sludge accumulation portion 26 and for producing biogas from wastewater.

It is important to note that anaerobic and anoxic digestion typically produces foul smelling and toxic gases. Accordingly, the full anaerobic or anoxic digestion mode is optionally preceded by aerobic digestion (to produce sludge) and is typically followed by an aerobic digestion mode finishing step as described above to eliminate toxic and foul-smelling gases prior to use or for disposal of the processed wastewater. In some embodiments, the modes are serially alternated a number of times: aerobic, anaerobic, aerobic, anaerobic and so on, as required.

Mixed Mode

In a third, mixed, mode, aerobic and anaerobic (or anoxic) digestions are performed simultaneously in digestion chamber 14. Specifically, both liquid-driving pumps 44*a* and 44*b* are activated, while gas inlet valve 58*b* of the lower mixing assembly 32*b* is in the closed state and gas inlet valve 58*a* of the upper mixing assembly 32*a* is in an open state. As a consequence, the contents of upper portion 16*a* of chamber 14 are aerated and mixed by the action of associated Venturi pumps (such as 36*a*) allowing for aerobic digestion thereof. In contrast, the contents of lower portion 16*b* of chamber 14 are mixed by the action of associated Venturi pumps (such as 36*b*) but since gas inlet valve 58*b* is closed, the contents of lower portion 16*b* of chamber 14 become increasingly anaerobic or anoxic, as described above. The aerobic digestion in upper portion 16*a* and/or the anaerobic/anoxic digestion in lower portion 16*b* is optionally aided by activating a respective heating pad 68 or by adding gas or liquid reagents by selectively opening a respective reagent valve 66 as desired. The relative volume of wastewater undergoing aerobic digestion compared to the volume of wastewater undergoing anaerobic digestion can be varied by changing the relative pumping rate of the respective liquid-driving pumps 44a and 44b.

The mixed mode is particularly useful for continuous processing of wastewater. Wastewater is primarily processed by aerobic digestion in upper portion 16a. Produced sludge settles to lower portion 16b to undergo anaerobic digestion so there is little sludge formation and efficient biogas formation. Foul smelling gases that are emitted by the anaerobic digestion rise to upper portion 16a to be immediately neutralized.

In an alternative embodiment, the entire chamber 14 is operated for aerobic digestion as described above to process wastewater by aerobic digestion at a maximal capacity. When a substantial amount of sludge accumulates in lower portion 16b, chamber 14 is operated so that wastewater and sludge in lower portion 16b undergoes anaerobic digestion to reduce the amount of sludge while the wastewater in upper portion 16a undergoes aerobic digestion allowing further processing of wastewater by aerobic digestion (at a reduced capacity) and to neutralize the foul smelling gases released by the anaerobic digestion.

Figure 3:
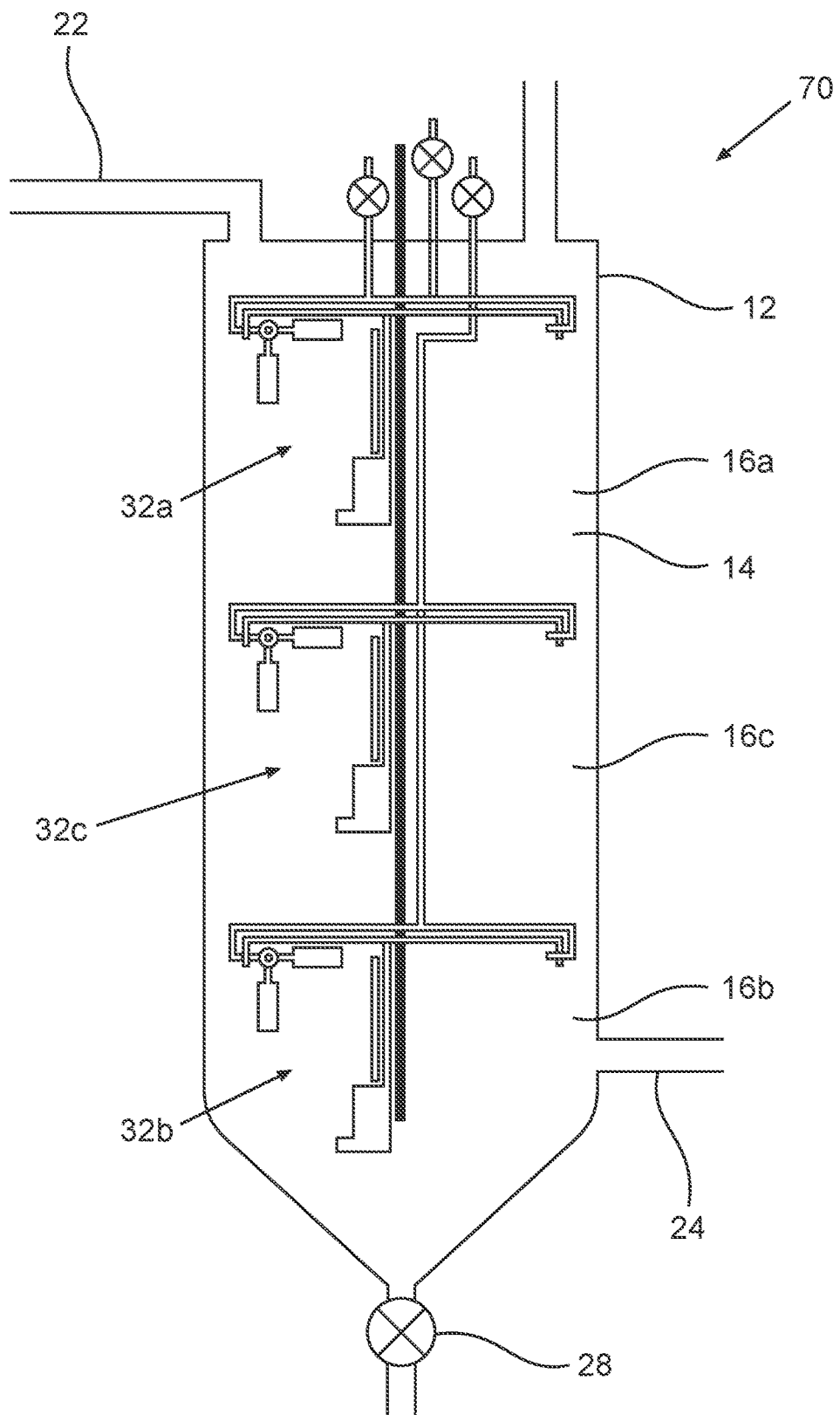
FIG. 3 is a schematic depiction of an embodiment of a device according to the teachings herein in side cross section.

An additional embodiment of a device according to the teachings herein, device 70, is schematically depicted in side cross section in FIG. 3. Device 70 has many of the same components as discussed above with reference to device 10, with two notable differences. A first notable difference is that chamber outlet 24 provides fluid communication from lower portion 16b of chamber 14. A second notable difference is the presence of a third mixing assembly 32c located between upper mixing assembly 32a and lower mixing assembly 32b, defining a middle portion 16c of digestion chamber 14.

Device 70 can be operated substantially as device 10, with the exception that processed wastewater is removed from lower portion 16b of chamber 14 through chamber outlet 24. During operation, aerobic or anaerobic digestion is independently maintained or changed in portions 16a, 16b and 16c.

A particular mode of operation that can be implemented using device 70 comprises simultaneous aerobic digestion in upper portion 16a, aerobic digestion in lower portion 16b and anaerobic (or anoxic) digestion in middle portion 16c. Toxic and foul smelling gases produced by anaerobic digestion in middle portion 16c are neutralized in upper portion 16a, while wastewater that enters chamber 14 through inlet 22 undergoes aerobic digestion in upper portion 16a, anaerobic digestion in middle portion 16c to digest sludge and undergoes aerobic digestion as a finishing step in lower portion 16b prior to use or disposal.

In some embodiments, during processing of wastewater, aerobic digestion is continuously maintained in upper portion 16a, anaerobic digestion is continuously maintained in lower portion 16b, and middle portion 16b is alternated between aerobic and anaerobic digestion.

The Venturi pump outlets of a device according to the teachings herein are directed in any suitable direction. In some preferred embodiments, the Venturi pump outlets are directed in a way relative to the inlet of a respective liquid-driving pump to encourage generation of a cyclical motion of liquid inside a corresponding portion of the chamber. In device 10 depicted in FIG. 1, Venturi pump outlets 42 are directed downwardly parallel to vertical axis 20 of chamber 14. In some embodiments, the Venturi pump outlets are directed upwardly parallel to the vertical axis of the chamber. In some embodiments, the Venturi pump outlets are directed perpendicular to the vertical axis of the chamber.

In device 10 depicted in FIG. 1 and in device 70 depicted in FIG. 3, each mixing assembly is provided with a dedicated liquid-driving pump to drive liquid through respective Venturi pumps so that the mixing assemblies are independently operable by independently activating and controlling the dedicated pump or pumps. In some embodiments, liquid is driven through the Venturi pumps of both mixing assemblies by shared liquid-driving pump or pumps. In such embodiments, the device is typically provided with differentially controllable valves allowing the relative amount of liquid driven through the different Venturi pumps of the different mixing assemblies to be controlled (including to be entirely prevented), thereby and allowing the mixing assemblies to be independently operable by independently opening and closing the valves associated with each mixing assembly.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A device suitable for performing chemical and/or biological reactions, comprising:
    a. a vessel defining at least one reaction chamber configured for holding liquids, said chamber having an upper portion, a lower portion and a vertical axis;
    b. at least one chamber inlet providing fluid communication into said chamber from outside said chamber;
    c. at least one chamber outlet providing fluid communication from inside said chamber to outside said chamber;
    d. an upper mixing assembly located inside said chamber; and
    e. a lower mixing assembly located inside said chamber, positioned below said upper mixing assembly,
    each said mixing assembly comprising a Venturi pump having a motive fluid inlet, an aspirate inlet and Venturi pump outlet, said Venturi pump configured for accepting liquid contents of a corresponding portion of said chamber into said motive fluid inlet as motive fluid and to expel fluid from said Venturi pump outlet back into said corresponding portion of said chamber,
    said device further comprising a gas line in fluid communication with an aspirate inlet of a Venturi pump of the upper mixing assembly,
    wherein said upper mixing assembly and said lower mixing assembly are independently operable.

2. The device of claim 1, wherein at least one Venturi pump outlet is directed perpendicularly to said vertical axis of said chamber.

3. The device of claim 1, wherein at least one Venturi pump outlet is directed parallel to said vertical axis of said chamber.

4. The device of claim 1, comprising at least one liquid-driving pump functionally associated with said upper mixing assembly, configured to drive liquid contents of said chamber into a said motive fluid inlet of a said Venturi pump of said upper mixing assembly.

5. The device of claim 4, wherein said liquid-driving pump functionally associated with said upper mixing assembly is an immersible liquid pump located inside said chamber.

6. The device of claim 4, further comprising a controllable valve having at least two states:
 an open state allowing flow of liquid from said liquid-driving pump to said motive fluid inlet of said Venturi pump to said upper mixing assembly; and
 a closed state preventing flow of liquid from said liquid-driving pump to said motive fluid inlet of said Venturi pump to said upper mixing assembly.

7. The device of claim 4, further comprising at least one liquid-driving pump functionally associated with said lower mixing assembly, configured to drive liquid contents of said chamber into a said motive fluid inlet of a said Venturi pump of said lower mixing assembly,
 wherein at least one of said at least one liquid-driving pump associated with said upper mixing assembly is different from at least one of said at least one liquid-driving pump associated with said lower mixing assembly.

8. The device of claim 7, wherein said at least one liquid-driving pump associated with said upper mixing assembly and said at least one liquid-driving pump associated with said lower mixing assembly are separately activatable.

9. The device of claim 1, comprising at least one liquid-driving pump functionally associated with said lower mixing assembly, configured to drive liquid contents of said chamber into a said motive fluid inlet of a said Venturi pump of said lower mixing assembly.

10. The device of claim 9, further comprising at least one liquid-driving pump functionally associated with said upper mixing assembly, configured to drive liquid contents of said chamber into a said motive fluid inlet of a said Venturi pump of said upper mixing assembly,
 wherein at least one of said at least one liquid-driving pump associated with said upper mixing assembly is also at least one of said at least one liquid-driving pump associated with said lower mixing assembly.

11. The device of claim 9, further comprising a controllable valve having at least two states:
 an open state allowing flow of liquid from said liquid-driving pump to said motive fluid inlet of said Venturi pump of said lower mixing assembly; and
 a closed state preventing flow of liquid from said liquid-driving pump to said motive fluid inlet of said Venturi pump of said lower mixing assembly.

12. The device of claim 1, further comprising an upper temperature controller, located within or in immediate proximity to said upper portion of said chamber to control the temperature of liquid contents of said chamber located in proximity of said upper mixing assembly without substantially affecting the temperature of contents of said chamber located in proximity of said lower mixing assembly.

13. The device of claim 1, further comprising a lower temperature controller, located within or in immediate proximity to said lower portion of said chamber to control the temperature of liquid contents of said chamber located in proximity of said lower mixing assembly without substantially effecting the temperature of contents of said chamber located in proximity of said upper mixing assembly.

14. A method of simultaneously performing at least two chemical and/or biological reactions under different conditions in a single reaction chamber, comprising:
 placing a device of claim 1 so that said vertical axis is at an angle within 45° of parallel to a gravity vector so that said upper portion is above said lower portion;
 placing at least one liquid inside said reaction chamber of said vessel so that both said upper portion and said lower portion contain a said liquid, wherein a said liquid in said upper portion has a different density than a said liquid in said lower portion; and
 performing at least one of:
  operating said upper mixing assembly to circulate a said liquid in said upper portion of said chamber without substantially circulating liquid in said lower portion of said chamber; and
  operating said lower mixing assembly to circulate a said liquid in said lower portion of said chamber without substantially circulating liquid in said upper portion of said chamber,
 thereby performing a first reaction in said upper portion of said reaction chamber and a second reaction in said lower portion of said reaction chamber, wherein conditions of said first reaction are different than the conditions of said second reaction.

15. The method of claim 14, wherein said angle is within 30° of perpendicular to a gravity vector.

16. The method of claim 14, wherein said first mixing assembly and said second mixing assembly are operated differently, thereby leading to said different reaction conditions in said upper portion and said lower portion.

17. The method of claim 16, wherein said different operation comprises at least one of:
 addition of a different liquid to one of said upper portion and said lower portion;
 addition of a different gas to one of said upper portion and said lower portion; and
 maintaining a temperature in said upper portion different than a temperature in said lower portion.

18. A method of simultaneously performing at least two chemical and/or biological reactions under different conditions in a single reaction chamber, comprising:
 placing a device of claim 1 so that said vertical axis is at an angle within 45° of parallel to a gravity vector so that said upper portion is above said lower portion;
 placing at least one liquid inside said reaction chamber of said vessel so that both said upper portion and said lower portion contain a said liquid; and
 performing at least one of:
  operating said upper mixing assembly to circulate a said liquid in said upper portion of said chamber without substantially circulating liquid in said lower portion of said chamber; and
  operating said lower mixing assembly to circulate a said liquid in said lower portion of said chamber without substantially circulating liquid in said upper portion of said chamber,
 thereby performing a first reaction in said upper portion of said reaction chamber and a second reaction in said lower portion of said reaction chamber, wherein said first mixing assembly and said second mixing assembly are operated differently, thereby leading to said different reaction conditions in said upper portion and said lower portion.

19. The method of claim 18, wherein said angle is within 30° of perpendicular to a gravity vector.

20. The method of claim 18, wherein said different operation comprises at least one of:
   addition of a different liquid to one of said upper portion and said lower portion;
   addition of a different gas to one of said upper portion and said lower portion; and
   maintaining a temperature in said upper portion different than a temperature in said lower portion.

21. A method of simultaneously performing at least two chemical and/or biological reactions under different conditions in a single reaction chamber, comprising:
   placing a device of claim 1 so that said vertical axis is at an angle within 45° of parallel to a gravity vector so that said upper portion is above said lower portion;
   placing at least one liquid inside said reaction chamber of said vessel so that both said upper portion and said lower portion contain a said liquid, wherein a said liquid in said upper portion has a different gas content than a said liquid in said lower portion; and
   performing at least one of:
      operating said upper mixing assembly to circulate a said liquid in said upper portion of said chamber without substantially circulating liquid in said lower portion of said chamber; and
      operating said lower mixing assembly to circulate a said liquid in said lower portion of said chamber without substantially circulating liquid in said upper portion of said chamber,
   thereby performing a first reaction in said upper portion of said reaction chamber and a second reaction in said lower portion of said reaction chamber, wherein conditions of said first reaction are different than the conditions of said second reaction.

22. The method of claim 21, wherein said angle is within 30° of perpendicular to a gravity vector.

23. The method of claim 21, wherein a said liquid in said upper portion has a different density than a said liquid in said lower portion.

24. The method of claim 21, wherein said first mixing assembly and said second mixing assembly are operated differently, thereby leading to said different reaction conditions in said upper portion and said lower portion.

25. The method of claim 24, wherein said different operation comprises at least one of:
   addition of a different liquid to one of said upper portion and said lower portion;
   addition of a different gas to one of said upper portion and said lower portion; and
   maintaining a temperature in said upper portion different than a temperature in said lower portion.

26. A device suitable for performing chemical and/or biological reactions, comprising:
   a. a vessel defining at least one reaction chamber configured for holding liquids, said chamber having an upper portion, a lower portion and a vertical axis;
   b. at least one chamber inlet providing fluid communication into said chamber from outside said chamber;
   c. at least one chamber outlet providing fluid communication from inside said chamber to outside said chamber;
   d. an upper mixing assembly located inside said chamber; and
   e. a lower mixing assembly located inside said chamber, positioned below said upper mixing assembly,
   each said mixing assembly comprising a Venturi pump having a motive fluid inlet, an aspirate inlet and Venturi pump outlet, said Venturi pump configured for accepting liquid contents of a corresponding portion of said chamber into said motive fluid inlet as motive fluid and to expel fluid from said Venturi pump outlet back into said corresponding portion of said chamber, said device further comprising a gas line in fluid communication with an aspirate inlet of said Venturi pump of said upper mixing assembly,
   the device further comprising:
      at least one liquid-driving pump functionally associated with said upper mixing assembly, configured to drive liquid contents of said chamber into a said motive fluid inlet of a said Venturi pump of said upper mixing assembly; and
      at least one liquid-driving pump functionally associated with said lower mixing assembly, configured to drive liquid contents of said chamber into a said motive fluid inlet of a said Venturi pump of said lower mixing assembly,
   wherein at least one of said at least one liquid-driving pump associated with said upper mixing assembly is different from at least one of said at least one liquid-driving pump associated with said lower mixing assembly.

27. The device of claim 26, wherein at least one Venturi pump outlet is directed perpendicularly to said vertical axis of said chamber.

28. The device of claim 26, wherein at least one Venturi pump outlet is directed parallel to said vertical axis of said chamber.

29. The device of claim 26, wherein said liquid-driving pump associated with said upper mixing assembly is an immersible liquid pump located inside said chamber.

30. The device of claim 26, wherein at least one of said at least one liquid-driving pump associated with said upper mixing assembly is also at least one of said at least one liquid-driving pump associated with said lower mixing assembly.

31. The device of claim 26, further comprising a controllable valve having at least two states:
   an open state allowing flow of liquid from said liquid-driving pump to said motive fluid inlet of said Venturi pump of said lower mixing assembly; and
   a closed state preventing flow of liquid from said liquid-driving pump to said motive fluid inlet of said Venturi pump of said lower mixing assembly.

32. The device of claim 26, further comprising a controllable valve having at least two states:
   an open state allowing flow of liquid from said liquid-driving pump to said motive fluid inlet of said Venturi pump to said upper mixing assembly; and
   a closed state preventing flow of liquid from said liquid-driving pump to said motive fluid inlet of said Venturi pump to said upper mixing assembly.

33. The device of claim 26, wherein said at least one liquid-driving pump associated with said upper mixing assembly and said at least one liquid-driving pump associated with said lower mixing assembly are separately activatable.

34. The device of claim 26, further comprising an upper temperature controller, located within or in immediate proximity to said upper portion of said chamber to control the temperature of liquid contents of said chamber located in proximity of said upper mixing assembly without substantially affecting the temperature of contents of said chamber located in proximity of said lower mixing assembly.

35. The device of claim 26, further comprising a lower temperature controller, located within or in immediate proximity to said lower portion of said chamber to control the temperature of liquid contents of said chamber located in proximity of said lower mixing assembly without substantially effecting the temperature of contents of said chamber located in proximity of said upper mixing assembly.

36. The device of claim 26, wherein said upper mixing assembly and said lower mixing assembly are independently operable.

* * * * *